United States Patent
Helle et al.

(10) Patent No.: US 8,337,383 B2
(45) Date of Patent: Dec. 25, 2012

(54) SEED-CARTRIDGE BARREL ASSEMBLER

(75) Inventors: Kevin Helle, Bartlett, IL (US); Jay Reed, Elk Grove village, IL (US)

(73) Assignee: Medi-Physics, Inc., Princeton, NJ (US)

( * ) Notice: Subject to any disclaimer, the term of this patent is extended or adjusted under 35 U.S.C. 154(b) by 855 days.

(21) Appl. No.: 12/096,834

(22) PCT Filed: Dec. 15, 2006

(86) PCT No.: PCT/US2006/062158
§ 371 (c)(1),
(2), (4) Date: Jun. 10, 2008

(87) PCT Pub. No.: WO2007/070871
PCT Pub. Date: Jun. 21, 2007

(65) Prior Publication Data
US 2008/0300446 A1   Dec. 4, 2008

(51) Int. Cl.
*A61N 5/00* (2006.01)
(52) U.S. Cl. .............................. 600/7; 600/1
(58) Field of Classification Search ............... 600/1, 3, 600/7, 8; 604/164.07, 164.01; 269/43, 279, 269/309, 313, 314
See application file for complete search history.

(56) References Cited

U.S. PATENT DOCUMENTS

| | | | | |
|---|---|---|---|---|
| 4,106,907 A | * | 8/1978 | Charlton et al. | 436/541 |
| 4,822,331 A | * | 4/1989 | Taylor | 494/16 |
| 5,749,248 A | * | 5/1998 | Kim | 68/4 |
| 2005/0267319 A1 | * | 12/2005 | White et al. | 600/7 |
| 2007/0063406 A1 | * | 3/2007 | Soroka et al. | 269/309 |

FOREIGN PATENT DOCUMENTS

| | | |
|---|---|---|
| DE | 9108831 | 9/1991 |
| EP | 1524002 | 4/2005 |
| WO | 87/00788 | 2/1987 |
| WO | 03/063944 | 8/2003 |

OTHER PUBLICATIONS

PCT/US2006/062158 Int'l Search Report/Written Opinion dated Mar. 2007.

* cited by examiner

*Primary Examiner* — Charles A. Marmor, II
*Assistant Examiner* — Joshua D Lannu
(74) *Attorney, Agent, or Firm* — Robert F. Chisholm

(57) ABSTRACT

An assembler which limits the amount of torque that may be applied to a brachytherapy cartridge magazine when its cap is threaded onto same. The assembler is constructed so that the brachytherapy cartridge will rotate within the assembler before a destructive torque is applied while the cap and cartridge magazine are screwed together.

13 Claims, 5 Drawing Sheets

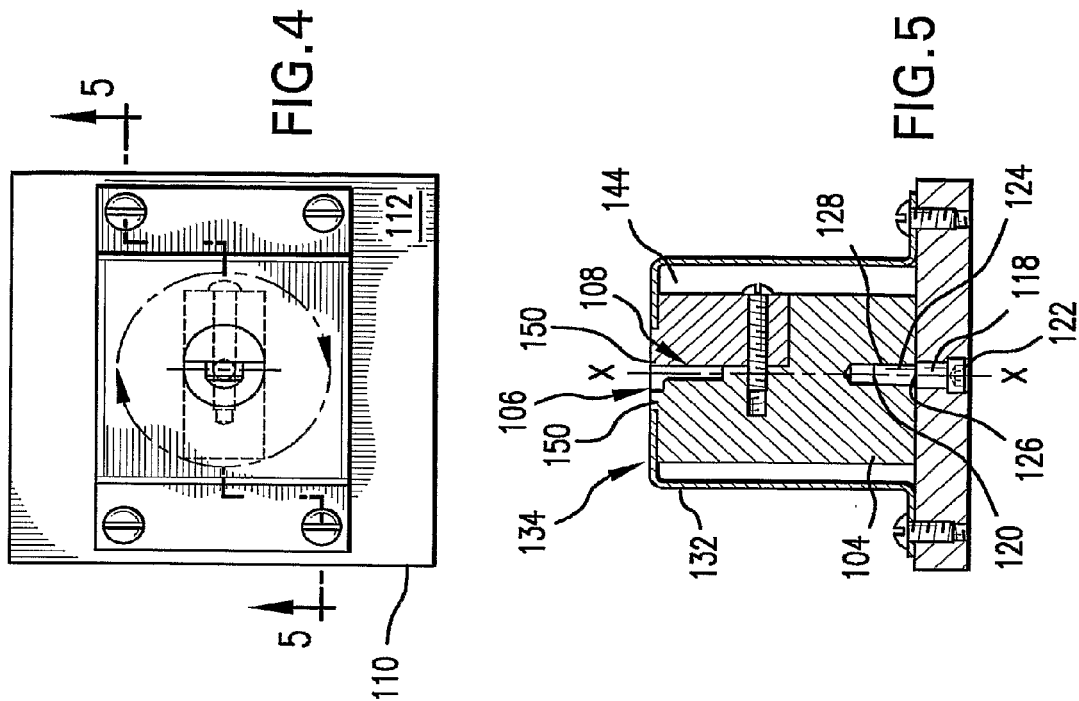
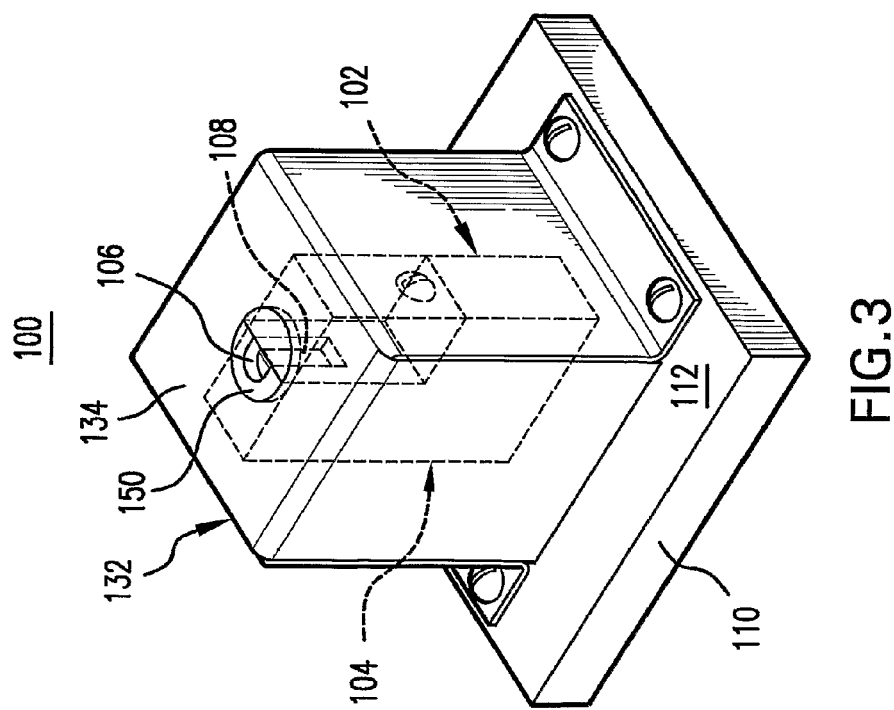

SEED-CARTRIDGE BARREL ASSEMBLER

FIELD OF THE INVENTION

The present invention relates to the field of brachytherapy equipment. More specifically, the present invention is directed to an assembler for preventing a destructive torque being applied to a brachytherapy cartridge.

BACKGROUND OF THE INVENTION

Brachytherapy seed cartridges are provided with a number of radioactive brachytherapy seeds, e.g. I-125 or Pd-103 seeds, and used as a supply source of those seeds to be loaded into a seed applicator. The seed applicator is used to implant the seeds within a patient. FIGS. 1 and 2A-C depict a typical seed cartridge 10 manufactured and sold by Mick Radio-Nuclear Instruments, Inc. of Mount Vernon, N.Y., U.S.A. Cartridge 10 includes a magazine 12 and a cap 14. Magazine 12 includes an elongate seed channel 16 for receiving transversely-aligned brachytherapy seeds 18 and dispense aperture 20 from which the seeds are dispensed into the applicator. Cap 14 supports an elongate plunger 22 which is spring-biased to extend into channel 16 and urge the seeds 18 towards dispense aperture 20. Magazine 12 further includes an external helical thread 24 for mating with an internal helical thread, not shown, within cap 14. Cap 14 includes an external thread 26 to secure the assembled cartridge 10 in a V-block for steam sterilization.

To form a disposable, or single-use, cartridge 10, magazine 12 and cap 14 are typically made of a suitable plastic material capable of withstanding steam sterilization. Alternatively, cap 14 may be formed from stainless steel or brass in order to provide additional shielding. This later feature recognizes that a technician holding a cartridge component in each hand while threading the two components together, due to the proximity of the radioactive seeds to the technician's hands and fingers, presents exposure risks which should be minimized further.

Moreover, the art has seen instances of magazine 12 deforming and/or breaking when a technician applies a tightening torque to cap 14 which exceeds the torsional limit of the plastic magazine 12. Typically, the magazine body is deformed so as to pinch on channel 16 and cause a functionality failure where the seeds will not descend properly under the spring tension of the plunger. The deformed or broken magazine 12 can also lose containment of the radioactive seeds, resulting in a loss of the loaded seeds and a potential hazard to personnel handling the cartridge.

SUMMARY OF THE INVENTION

In view of the needs of the prior art, the present invention provides an assembler which limits the amount of torque that may be applied to a brachytherapy cartridge during assembly when its cap is threaded on. The assembler is constructed so that the brachytherapy cartridge will rotate within the assembler before a destructive torque is applied by the cap to the magazine while the cap and magazine are screwed together. The assembler may be operated, and the cartridge thus assembled, using only one hand. The assembler includes a cartridge-receiving block having an elongate block body defining a cartridge aperture and an elongate cartridge receptacle extending about the longitudinal axis of the body. The longitudinal axis of the body is desirably closely aligned with the longitudinal axis of rotation of both the body and the cartridge. The cartridge receptacle extends in fluid communication with the cartridge aperture. The cartridge aperture and cartridge receptacle are sized and shaped to receive a portion of the cartridge magazine therein so as to allow the threaded assembly of a the cartridge cap assembly to the magazine. The block may rotate about the longitudinal axis. As the cap is threaded to complete the cartridge, the block body and the cartridge will begin to rotate about the axis before a damaging torque is applied from the cap to the cartridge. The assembler may include a planar base on which the block is rotationally mounted. Additionally or alternatively, the assembler may include a housing within which the block may rotate.

BRIEF DESCRIPTION OF THE DRAWINGS

FIG. 3 depicts a brachytherapy seed cartridge assembler of the present invention.

FIG. 4 is a top elevational view of the assembler of FIG. 3.

FIG. 5 is a cross-sectional view of the assembler of FIG. 3 taken through the line 5-5 of FIG. 4.

DETAILED DESCRIPTION OF THE PREFERRED EMBODIMENT

Figure 1:
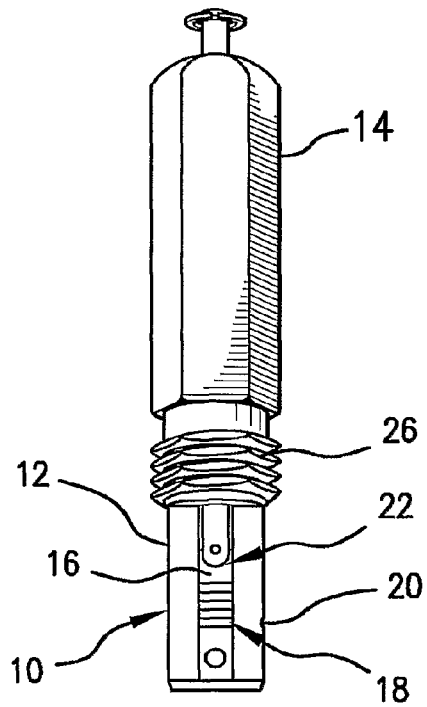
FIG. 1 depicts a brachytherapy seed cartridge to be assembled using the present invention.
Figure 2A:
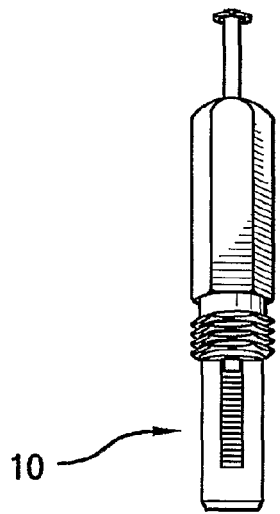
FIG. 2A depicts the brachytherapy seed cartridge of FIG. 1 showing the magazine filled with brachytherapy seeds.
Figure 2B:
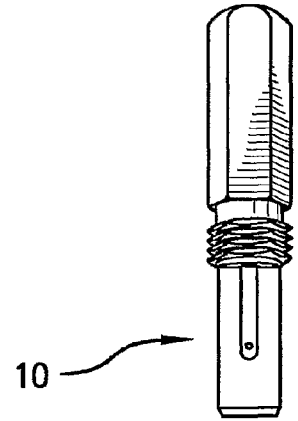
FIG. 2B depicts the brachytherapy seed cartridge of FIG. 1 showing the magazine empty of brachytherapy seeds.
Figure 2C:
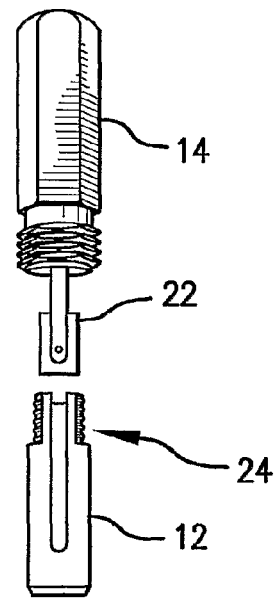
FIG. 2C depicts the brachytherapy seed cartridge of FIG. 1 with the cap separated from the magazine.

FIGS. 3-5 depicts a seed cartridge assembler 100 of the present invention. The components of assembler 100 are desirably formed from stainless steel although other suitable materials may alternatively be used. Assembler 100 includes a cartridge-receiving block 102, shown in phantom lines in FIG. 3, having an elongate block body 104 defining a cartridge aperture 106 and an elongate cartridge receptacle 108 extending about the longitudinal axis x of body 104. Cartridge receptacle 108 extends in fluid communication with cartridge aperture 106. Furthermore, cartridge aperture 106 and cartridge receptacle 108 are sized and shaped to receive at least a portion of a magazine 12 therein so as to expose the tread 24 of magazine 12 and to thereby allow the threaded assembly of cartridge cap 14 to magazine 12. The depth of cartridge receptacle 108 may be selected according to the number of seeds which are typically to be loaded into magazine 12, so as to expose the uppermost seed and provide a visual cue that the correct number of seeds are loaded into the magazine prior to threading cap 14 thereon.

Figure 7:
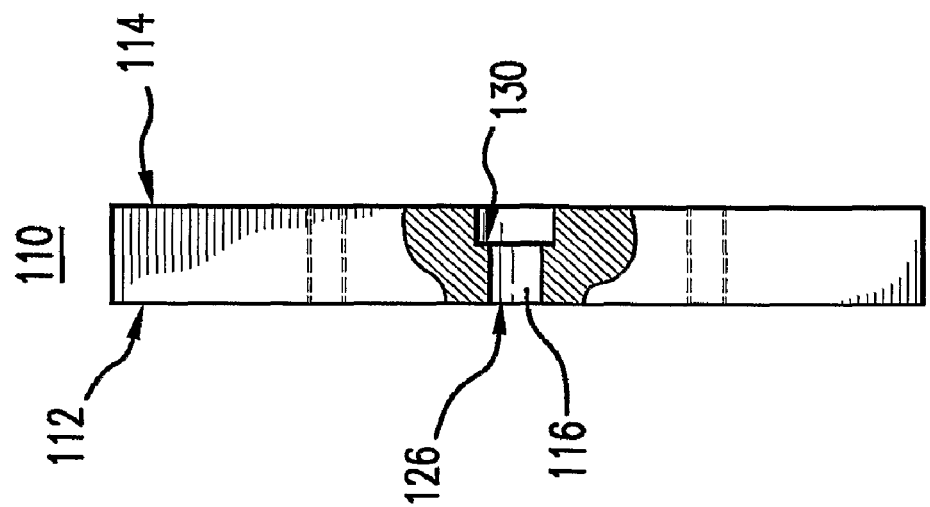
FIGS. 6 and 7 depict the base of the assembler of FIG. 3.
Figure 6:
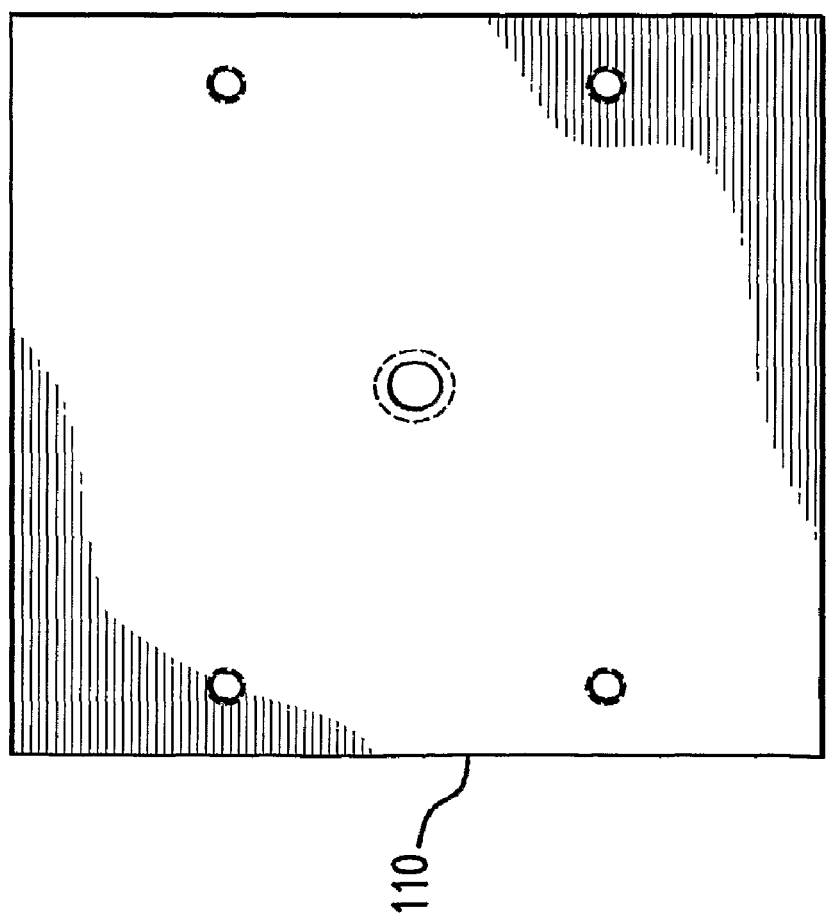

Assembler 12 also includes planar base 110 on which block 102 may rotate about longitudinal axis x. With additional reference to FIGS. 6 and 7, planar base 110 includes opposed major surfaces 112 and 114 and a stepped passageway 116 extending therebetween. Passageway accommodates a pivot pin 118 having opposed free end 120 and head 122 and an elongate pin body 124 extending therebetween. Block body 106 defines a pin aperture 126 and an elongate pin receptacle 128 extending about longitudinal axis x. Pin receptacle 128 extends in fluid communication with pin aperture 126 and is positioned in overlying registry with passageway 116 of base 110. Pivot pin head 122 seats against step 130 in base 110 and pin free end 120 is received within pin receptacle 128.

Figure 8:
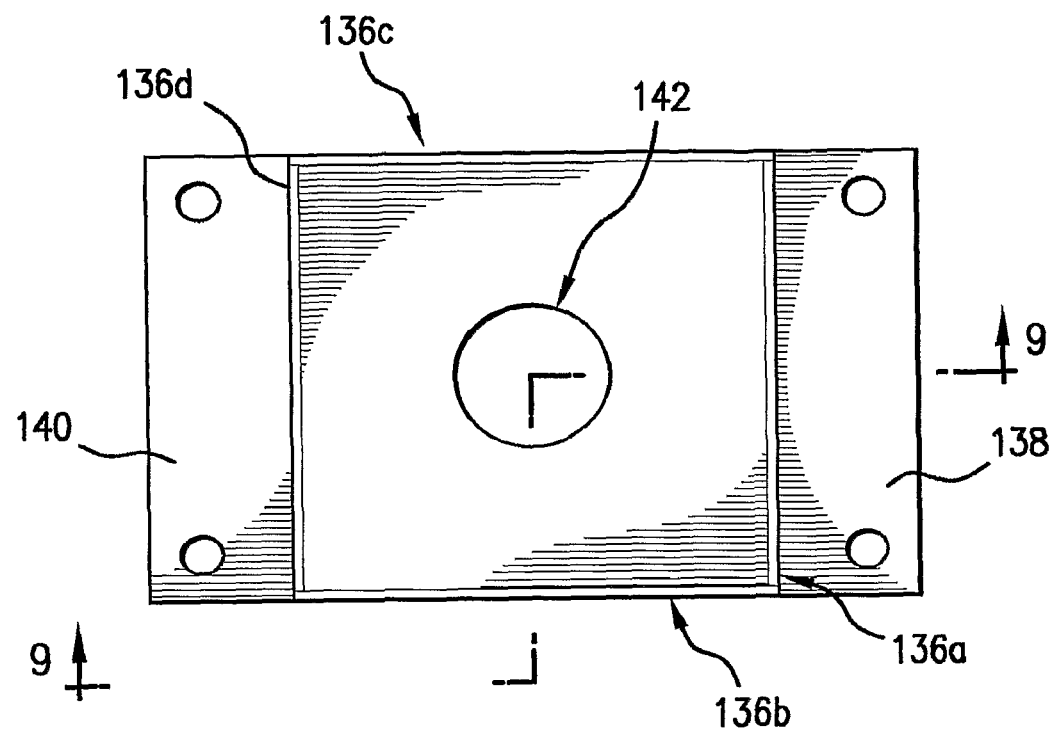
FIGS. 8 and 9 depict the housing of the assembler of FIG. 3.
Figure 9:
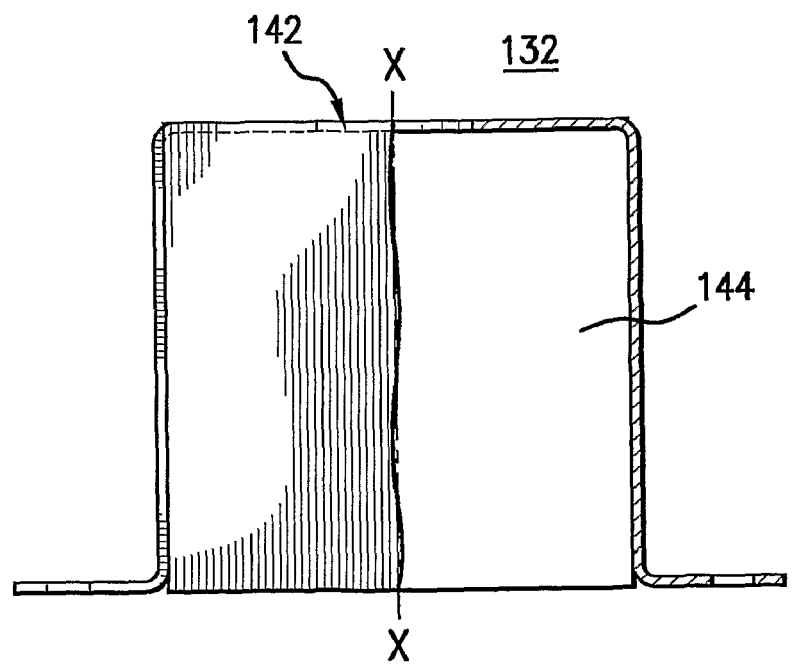

Assembler 110 further includes a housing 132 affixed to base 110. Housing 132 is desirably formed from stainless steel or another suitable radiation shielding material. With further reference to FIGS. 8 and 9, housing 132 includes a transversely-extending planar cover surface 134 supporting perimetrically-descending elongate planar walls 136a-d. Walls 136a and 136d further include flanges 138 and 140 for secure fastening of housing 132 to base 110 so that walls 136a-d are upstanding from base 110. Cover 134 of housing 132 defines a housing aperture 142 in fluid communication with cartridge aperture 106 and cartridge receptacle 108. Block 102 and cover 132 are desirably coplanar across housing aperture 142. Housing 132 further defines a block cavity 144 within which cartridge block 102 may rotate about axis x.

Figure 10:
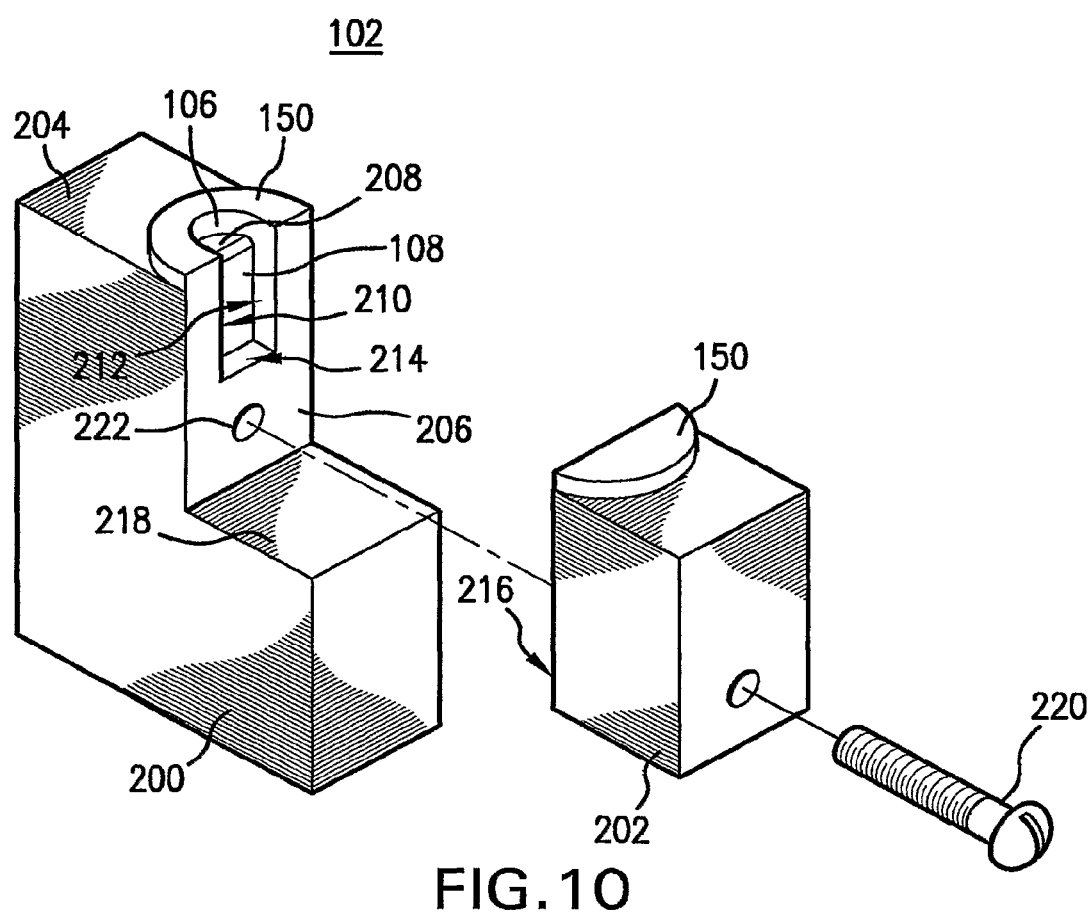
FIG. 10 is an exploded view of the cartridge-receiving block of the assembler of FIG. 3.

As particularly shown in FIGS. 3, 5 and 10, block body 102 includes cylindrical projection 150 defining cartridge aperture 106 that is coextensive with housing aperture 142 so as to prevent a loose brachytherapy seed from passing between housing cover 134 and block body 102.

With particular reference to FIG. 10, block body 102 includes an elongate rectangular body 200 and a corner cap 202 forming an upper quadrant thereof. Desirably, block body 102 is first machined to provide cylindrical projection 150 on a top surface 204. Projection 150 desirably being formed with dimensions which allow it to extend flush with cover surface 134 of housing 132 and in sliding abutment with housing 132 at aperture 142. Corner cap 202 is then cut away from body 200 to allow cartridge aperture 106 and cartridge receptacle 108 to be machined into an exposed face 206. Cartridge receptacle 108 is further defined by a transversely-extending planar step surface 208 and planar surfaces 210, 212, 214 adjacent thereto and descending away from cartridge aperture 106. Cartridge aperture 106 and cartridge receptacle 108 are fully defined by providing planar surface 216 of corner cap 202 against faces 206 and 218 of body 200. Cartridge receptacle 108 desirably conforms to the portion of magazine 12 of a cartridge 10 inserted therein. A bolt 220 is shown to extend through a bolt passageway defined by corner cap 202 and into an internally-threaded bolt receptacle 222 opening on face 206 to hold cap 202 to body 210. While corner cap 202 is shown bolted to body 200, it will be appreciated that any known fastening means may be used to reassemble the two components of block body 102.

Thus the present invention further contemplates that block 102 may take any shape. Additionally, the present invention further contemplates that a block of the present invention may be provided unconstrained, that is without a mounting plate or housing. Desirably, axis x of body 104 is closely aligned with one of the rotational axes of block 102 and the cartridge inserted therein so that when rotation of block 102 is caused by screwing the cap 14 to the magazine 12, any shear or non-axial loads on the cartridge components are minimized. For example, by way of illustration and not of limitation, the present invention further contemplates that the assembler includes an open cylindrical wall mounted on the planar base. The cylindrical wall would extend about block 102 so as to allow block 102 to rotate about axis x. It is further contemplated that a cylindrical wall could receive a cylindrical block defining the cartridge receptacle. Additionally, the cylindrical wall and the block are contemplated as being shaped so that the cylindrical wall positively holds the block against the base, so as to obviate the need for a pivot pin. And while cartridge receptacle 108 has been shown to closely conform to the portion of the cartridge 10 inserted therein, it is further contemplated that receptacle 108 may have any shape which ensures that block 102 will begin to rotate before the tightening of cap 14 onto magazine 12 causes damage to the magazine. These and other modifications will be apparent to one of ordinary skill in the art as being within the scope of the present invention.

According to a method of using the present invention, a magazine 12 loaded with brachytherapy seeds 18 is inserted into cartridge receptacle 108. A cap 14 can then be assembled to magazine 12 by inserting the plunger 22 into channel 16 and threading cap 14 onto thread 24. As cap 14 is tightened onto magazine 12, block 102 will begin to rotate prior to the torque applied to cartridge 10 exceeding the structural limits of the body of magazine 12. Testing on Mick cartridges has determined that the torque applied between magazine 12 and cap 14 should be less than about 1 inch-pound. However, it is contemplated that the rotational inertia of the present invention may be selected to accommodate any brachytherapy seed cartridge having two components to be threadably mated.

Additionally, to lessen the exposure risk to the radioactive seeds in the magazine, the present invention allows a technician to assemble the cartridge components using only one hand. The loaded cartridge may be positioned within the assembler and the cap then brought upon the cartridge thread and screwed down into place. If the weight and inertia, or friction force between the base and the surface upon which it rests, are sufficient, the technician may perform this assembly using only one hand. The technician may also use their free hand to hold the assembler by the base while threading the cap onto the magazine. Alternatively still, the technician may use their free hand to grasp the assembler by the housing while threading the cap onto the magazine.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A torque-limiting seed-cartridge barrel assembler for a brachytherapy seed cartridge having a cartridge cap and a seed magazine containing a number of brachytherapy seeds, said assembler comprising:

a rotatable cartridge-receiving block comprising an elongate block body defining a cartridge aperture and an elongate cartridge receptacle extending about the longitudinal axis of said body, said cartridge receptacle being in fluid communication with said cartridge aperture, said cartridge aperture and receptacle sized and shaped to receive a portion of the seed magazine therein so as to allow the threaded assembly of the cartridge cap to the magazine and said cartridge body able to rotate about an axis of rotation when said cartridge cap has been assembled to the magazine, wherein said cartridge receptacle is further defined by a transversely-extending planar step surface and four planar surfaces adjacent thereto and descending away from said cartridge aperture, and a housing comprising an elongate housing defining a block cavity into which said block body is received, said housing defining a housing aperture, wherein the portion of said block body defining said cartridge aperture is coextensive with said housing aperture so as to prevent a loose brachytherapy seed from passing between said housing and said block body.

2. The assembler of claim 1, wherein said longitudinal axis of said body aligns with the axis of rotation of said body.

3. The assembler of claim 1, wherein said longitudinal axis of said body aligns with the axis of rotation of the cartridge, a portion of which cartridge has been inserted into said cartridge receptacle.

4. The assembler of claim 1, further comprising a planar base on which said block may rotate about said longitudinal axis.

5. The assembler of claim 4, further comprising an elongate pivot pin, wherein said block body defines a pin aperture and an elongate pin receptacle extending about said longitudinal axis of said block body, said pin receptacle in fluid communication with said pin aperture, and wherein said base defines an elongate pin passageway opening on at least one major surface of said base, said pivot pin extending within said pin receptacle and said pin passageway.

6. The assembler of claim 1 further comprising a base, wherein the housing is affixed to said base, said housing comprising an upstanding wall defining a housing aperture in fluid communication with said cartridge aperture and cartridge receptacle of said block body, said upstanding wall further defining a block cavity within which said cartridge block may rotate about said longitudinal axis.

7. The assembler of claim 6, wherein said housing is formed from a radiation-shielding material.

8. The assembler of claim 6, wherein said housing further comprises a transversely-oriented planar housing cover defining said housing aperture.

9. The assembler of claim 8, wherein said housing cover and the portion of said block body defining said cartridge aperture are coplanar.

10. The assembler of claim 8, wherein said housing cover comprises a planar rectangular body and said upstanding wall comprises four planar rectangular walls perimetrically depending from said housing cover.

11. The assembler of claim 1, wherein said block body further comprises an elongate rectangular body.

12. The assembler of claim 1, wherein said cartridge receptacle is further defined by said body to substantially conform to the portion of a cartridge inserted therein.

13. A torque-limiting seed-cartridge barrel assembler which limits the amount of torque that may be applied to a brachytherapy cartridge magazine when its cartridge cap is threaded thereon, said assembler comprising an elongate rotatable cartridge receiving block defining a receptacle for receiving a portion of the cartridge magazine, wherein said cartridge receptacle is further defined by a transversely-extending planar step surface and four planar surfaces adjacent thereto and descending away from said cartridge aperture, said block and receptacle extending about an axis of rotation about which both are rotatable, said assembler constructed so that said receiving block will rotate about said axis or rotation at a lower torque than a destructive torque which may be applied from a cap to a magazine received in said receptacle as the cap and magazine are threaded together, said assembler further comprising a housing for receiving said block, said housing defining a housing aperture and said block defining said receptacle is coextensive with said housing aperture.

* * * * *